[54] METHOD FOR THE TREATMENT OF ANXIETY

[76] Inventor: David F. Horrobin, 110 Pine Ave. West, Montreal, Canada, H2W 1R7

[21] Appl. No.: 69,493

[22] Filed: Aug. 24, 1979

[30] Foreign Application Priority Data

Sep. 1, 1978 [GB] United Kingdom ............ 35313/78

[51] Int. Cl.³ .......................................... A61K 31/505
[52] U.S. Cl. ................................................. 424/251
[58] Field of Search ....................................... 424/251

Primary Examiner—Stanley J. Friedman
Attorney, Agent, or Firm—Schwartz, Jeffery, Schwaab, Mack, Blumenthal & Koch

[57] ABSTRACT

A method for the treatment of anxiety which consists of administering dipyridamole or imidazole or a derivative thereof. It has been found that known anti-anxiety agents appear to act as competitive antagonists of thromboxane A2 (TXA2), and it is therefore believed that dipyridamole and imidazole, which inhibit the formation of TXA2, will be effective in the treatment of anxiety.

3 Claims, No Drawings

METHOD FOR THE TREATMENT OF ANXIETY

This invention relates to a novel treatment for anxiety, primarily, but not exclusively, in the treatment of anxiety in humans and to pharmaceutical compositions for use therein.

Benzodiazepines, such as diazepam and chlordiazepoxide are in widespread use in the treatment and control of anxiety states in humans, but their mechanism of action is not at present understood.

Thromboxane A2 (TXA 2) is a substance which is related to prostaglandins. Thus, the biosynthesis of prostaglandins is believed to involve the synthesis of intermediate prostaglandin endoperoxides from arachidonic acid or membrane phospholipids. Prostaglandins are produced from the intermediate endoperoxides, simultaneously with the production of TXA2. It is believed that TXA2 plays an important part in this biosynthetic system as it appears to act as a regulator in the formation of arachidonic acid from dihomo-γ-linolenic acid and membrane phospholipids and in the conversion of arachidonic acid to prostaglandins.

Research which the present inventor has effected (see Neuroscience Letters 7 (1978) 31-34) has shown that the known anti-anxiety agents, diazepam and chlordiazepoxide, appear to have the characteristics of a competitive antagonist of TXA2. This finding has led to the belief that substances which will inhibit the formation of TXA2 will be effective in the treatment of anxiety.

Side effects which are most frequently associated with benzodiazepines include drowsiness, dizziness, fatigue, apathy, constipation, irritability and ataxia, other side effects being less frequent. There is also a danger of drug dependance occuring when these drugs are administered over relatively prolonged periods. There is therefore a need for chemotherapeutic agents in the treatment of anxiety which at least partially avoid these side effects.

The present inventor has found that dipyridamole (2,6-bis(diethanolamino)-4,8-dipiperidino pyrimido [5,4-d] pyrimidine) is a powerful inhibitor of the biosynthesis of TXA2 from intermediate prostaglandin endoperoxides (see Prostaglandins 14 (1977) 607-9), and has now surprisingly found that this substance is effective in the treatment of anxiety.

Thus, according to one feature of the present invention there is provided a method for the treatment of anxiety in a subject which method comprises administering to said subject an effective amount of dipyridamole.

The dipyridamole may be administered to the subject as a pharmaceutical composition comprising the dipyridamole in association with a pharmaceutical carrier or excipient. Such pharmaceutical compositions are conveniently administered in forms suitable for oral, rectal or parenteral administration, such as, for example, tablets, capsules, powders, granulates, solutions, syrups, elixirs, suppositories and forms adapted to supply a sustained release of active ingredient. These forms may be prepared by methods which are conventional to the pharmaceutical art.

The compositions for use in the treatment according to the invention are preferably in the form of dosage units.

I have found that a suitable daily dosage of dipyridamole for control of anxiety attacks in disturbed subjects is from 25 to 1000 mg, e.g. 25 to 400 mg, the precise dosage depending, of course, on the particular condition of the subject being treated. If desired the daily dosage may be divided to give for example 2, 3 or 4 equal doses. My tests have indicated that 4 doses of about 12.5 mg of dipyridamole per day by an oral route may be sufficient to control anxiety attacks in subjects attempting to stop smoking.

The dosages which I have found to be generally acceptable in the treatment of anxiety by the administration of dipyridamole are significantly lower than those which have been indicated for the known uses of dipyridamole. Thus, according to a further feature of the invention there is provided a pharmaceutical composition for oral administration comprising a dosage unit of from 5 to 20 mg of dipyridamole in association with a pharmaceutical carrier or excipient. Conveniently the dosage unit contains about 12.5 mg of dipyridamole.

Other substances which have been shown to have an inhibitory effect on the biosynthesis of TXA2 and are therefore indicated in the treatment of anxiety include imidazole and derivatives thereof which are substituted at the 1-position by a $C_1$ to $C_{15}$ alkyl, aryl or aralkyl group.

Thus, according to a further aspect of the present invention there is provided a method for the treatment of anxiety in a subject which method comprises administering to said subject an effective amount of imidazole or a derivative thereof substituted at the 1-position by a $C_1$ to $C_{15}$ alkyl, aryl or aralkyl group.

Derivatives of imidazole which have been found to have a powerful inhibitory effect on TXA2 synthesis and are therefore indicated in the treatment of anxiety, include imidazole substituted at the 1-position by a methyl, ethyl, propyl, butyl, pentyl, nonyl, decyl, dodecyl, benzyl or 2-isopropylphenyl group.

Imidazole and its 1-substituted derivatives are conveniently administered in the treatment of anxiety in the form of pharmaceutical compositions additionaly containing pharmaceutical carriers and excipients. Such compositions may be in forms suitable for oral, rectal or parenteral administration such as for example those mentioned above.

Powders for oral administration may be prepared by forming a homogeneous dispersion of the active material in an ingestible pulverulent solid carrier, either by mixing and grinding it with the carrier, or by first pasting the pulverised carrier with the active material itself, or with a solution of the material, and then drying. Examples of suitable inert materials for inclusion as the carrier are calcium carbonate, calcium silicate, talc, calcium sulphate, kaolin, hard paraffin, beeswax, kieselguhr and magnesium stearate. These can be replaced or supplemented by binders such as sugar, starch, lactose and pectin. Flavour can be imparted to the powder by incorporation of sugar and/or aromatic substances such as soluble cocoa powder. When the pulverulent solid carrier is pasted with a solution of the desired active material, the solvents employed may include water, alcohol, chloroform and sorbitol, as may be appropriate.

Tablets may be prepared by compressing the powders just described into coherent shapes of the appropriate size. To facilitate the manufacturing operation before compression the powders may advantageously be mixed also with binders and/or lubricants, such as starch, pectin, gelatin, gum arabic, methylcellulose, carboxyl-methyl cellulose (preferably in the form of its sodium salt), talc, stearic acid and magnesium stearate, if these are not already present. The coherent tablets thus formed may be coated, for example with sugar to improve their appearance, taste and durability, and may, moreover, be scored to facilitate administration of smaller doses, if desired.

Capsules may be prepared by enclosing the active ingredient, if desired microencapsulated under a nitrogen atmosphere, within a casing or sheath formed of gelatin, glycogelatin or other suitable material. The nature of this material is chosen in relation to the point in the digestive system at which it is desired to release the active material. It is conveniently either of melting point less than body temperature, or soluble in gastric juices, thus, for example, at pH's of 2 or less, or 9 or more.

Syrups and elixirs may be prepared by dissolving or suspending the active material in aqueous liquid media, which may contain a sweetening agent such as a sugar, saccharin or a polyhydric alcohol like glycerol or sorbitol, or another flavouring agent, such as alcohol, chloroform, citrates, or of course both. In the case of suspensions, surface-active agents such as glyceryl monostearate, aluminium monostearate and/or ethyl oleate may be incorporated to maintain the suspension, and solubilizing agents may be employed in solutions, together with suitable co-solvents such as alcohols, chloroform and trichloroethylene, if these are not already present. The thixotropy and viscosity of the liquid medium may be adjusted by the inclusion of appropriate amounts of pectin, gelatin, gum tragacanth, carboxy-methyl-cellulose, or agar-agar. Colourants may also be incorporated.

Injectable preparations may be prepared by forming solutions and/or suspensions in any of the usual sterile media, which may be oily or aqueous.

Preferably the preparations are rendered isotonic with the body fluids, and adjusted to the desired viscosity.

Advantageously a preservative is incorporated into the preparation.

The pharmaceutical compositions for use according to the invention for rectal administration can be in the form of suppositories which conveniently contain conventional carriers used for this purpose such as for example neutral fats or polyethylene glycol or derivatives thereof.

It will be understood that the absolute quantity of active ingredients present in any dosage unit should not exceed that appropriate to the rate and manner of administration to be employed but on the other hand should also desirably be adequate to allow the desired rate of administration to be achieved by a small number of doses. The rate of administration will moreover depend on the precise pharmacological action desired.

The following Examples illustrate the preparation of pharmaceutical compositions according to the invention which may be used in the treatment of anxiety:

EXAMPLE 1

Tablets

Each tablet contains:

| Dipyridamole | 12.5 mg |
|---|---|
| Lactose | 72.5 mg |
| Corn starch | 55 mg |
| Soluble starch | 7.0 mg |
| Magnesium stearate | 3.0 mg |
| | 140 mg |

The active ingredient and magnesium stearate are granulated with an aqueous solution of the soluble starch, the granulate is dried and admixed thoroughly with lactose and corn starch. The mixture is then pressed into tablets of 140 mg weight. Four tablets may be administered daily in the treatment of anxiety.

EXAMPLE 2

Capsules

Each capsule contains:

| Dipyridamole | 12.5 mg |
|---|---|
| lactose | 62.5 mg |
| Corn starch | 40.0 mg |
| talc | 10.0 mg |
| | 125.0 mg |

The ingredients are mixed well together and filled into gelatin capsules in the conventional manner. Four capsules may be administered daily in the treatment of anxiety.

I claim:

1. A method for the treatment of anxiety in a subject having an anxiety which method comprises administering to said subject an amount of dipyridamole effective to control said anxiety.

2. A method according to claim 1 wherein said dipyridamole is administered in a daily dosage of from 25 to 1000 mg.

3. A method according to claim 1 wherein said dipyridamole is administered in 4 doses per day of about 12.5 mg of dipyridamole.

* * * * *